United States Patent
Mukherjee et al.

(10) Patent No.: US 8,489,186 B2
(45) Date of Patent: Jul. 16, 2013

(54) DEVICES AND METHODS FOR TREATMENT OF MYOCARDIAL CONDITIONS

(75) Inventors: Rupak Mukherjee, Charleston, SC (US); Francis Spinale, Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 13/128,191

(22) PCT Filed: Nov. 5, 2009

(86) PCT No.: PCT/US2009/063387
§ 371 (c)(1),
(2), (4) Date: Jul. 15, 2011

(87) PCT Pub. No.: WO2010/054069
PCT Pub. Date: May 14, 2010

(65) Prior Publication Data
US 2011/0264156 A1 Oct. 27, 2011

Related U.S. Application Data

(60) Provisional application No. 61/112,662, filed on Nov. 7, 2008.

(51) Int. Cl.
*A61N 1/40* (2006.01)

(52) U.S. Cl.
USPC ..................................... 607/2; 607/50; 607/5

(58) Field of Classification Search
USPC .................................................. 607/2–9, 50
See application file for complete search history.

(56) References Cited

U.S. PATENT DOCUMENTS

| | | | |
|---|---|---|---|
| 5,814,079 A | 9/1998 | Kieval | |
| 6,071,303 A * | 6/2000 | Laufer | 607/96 |
| 6,556,872 B2 | 4/2003 | Hauck | |
| 6,560,489 B2 | 5/2003 | Hauck | |
| 7,039,467 B2 | 5/2006 | Hauck | |
| 7,113,830 B2 | 9/2006 | Hauck | |
| 7,139,607 B1 | 11/2006 | Shelchuk | |
| 8,219,210 B2 * | 7/2012 | Arcot-Krishnamurthy et al. | 607/116 |
| 2001/0031986 A1 | 10/2001 | Hauck | |
| 2002/0095188 A1 | 7/2002 | Mower | |
| 2003/0139779 A1 | 7/2003 | Sharma et al. | |
| 2003/0163168 A1 | 8/2003 | Hauck | |
| 2004/0215258 A1 | 10/2004 | Lovett et al. | |
| 2005/0043766 A1 | 2/2005 | Soykan et al. | |
| 2008/0234771 A1 | 9/2008 | Chinchoy et al. | |
| 2008/0234772 A1 * | 9/2008 | Shuros et al. | 607/11 |

OTHER PUBLICATIONS

PCT/US2009/063387, International Search Report, mailed Jan. 6, 2010 (2 pages).
PCT/US2009/063387, International Preliminary Report on Patentability, mailed May 19, 2011 (10 pages).
European Supplementary Search Report for European Application No. EP 09825405, issued Mar. 15, 2012 (5 pages).
Communication pursuant to Rules 70(2) and 70a(2) EPC for European Application No. EP 09825405, issued Apr. 13, 2012 (6 pages).

* cited by examiner

*Primary Examiner* — Carl H Layno
*Assistant Examiner* — Paula J Stice
(74) *Attorney, Agent, or Firm* — Meunier Carlin & Curfman, LLC

(57) ABSTRACT

Provided are devices and methods for treating a subject having a myocardial condition using sub-threshold electrical stimulation.

20 Claims, 15 Drawing Sheets

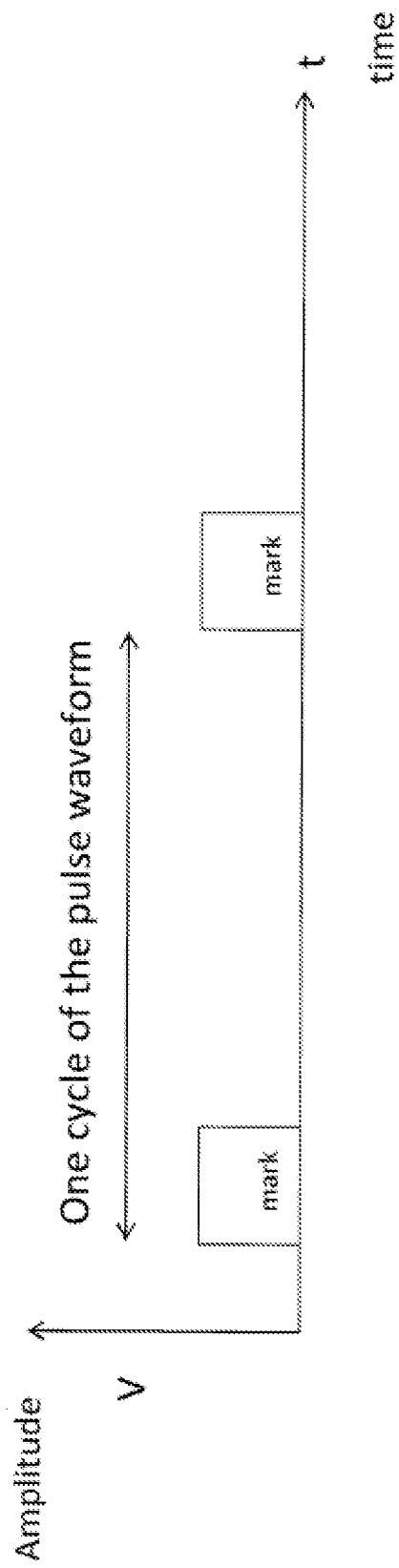

DEVICES AND METHODS FOR TREATMENT OF MYOCARDIAL CONDITIONS

This application claims the benefit of U.S. Provisional Application No. 61/112,662, filed Nov. 7, 2008. The entire disclosure of the prior application is hereby incorporated by reference.

This invention was made with government support under HL066029, HL045024, HL097012, HL048788 awarded by the National Institutes of Health. The United States government has certain rights in the invention.

BACKGROUND

Myocardial conditions lead to significant mortality and morbidity in populations throughout the world. For example, myocardial infarction can cause scar formation and left ventricular remodeling that can contribute to a poor prognosis. Individuals with acute coronary syndrome (ACS), arrhythmia, or coronary artery bypass grafts (CABG) can be at increased risk of cardiac ischemia, myocardial infarction and scarring that can lead to poor outcomes.

SUMMARY

Provided are devices and methods for treating a subject having, or at risk of developing, a myocardial condition. The devices and methods for treating a subject having a myocardial condition use sub-threshold electrical stimulation.

For example, provided is a method for treating a subject having a myocardial lesion comprising positioning an electrode relative to the myocardial lesion so that an electrical stimulus can be transmitted selectively to the myocardial lesion. A sub-threshold electrical stimulus can then be selectively transmitted to the myocardial lesion.

The lesion can be an area of myocardial ischemia. Thus, for example, further provided is a method for treating a subject having myocardial ischemia comprising positioning an electrode relative to an area of myocardial ischemia in the subject's heart so that an electrical stimulus can be transmitted selectively to the area of myocardial ischemia. A sub-threshold electrical stimulus can then be selectively transmitted to the area of myocardial ischemia.

The lesion can also be a cardiac arrhythmia. An example method for treating a subject having a cardiac arrhythmia comprises positioning an electrode relative to the subject's heart so that an electrical stimulus can be transmitted selectively to the myocardium at the anatomic origin of the arrhythmia. A sub-threshold electrical stimulus can then be selectively transmitted to the myocardium at the origin of the arrhythmia.

An example device for treating a subject having a myocardial lesion comprises a stimulus generator adapted to produce a sub-threshold electrical stimulus for transmission to the myocardial lesion. The example device can further comprise a stimulus electrode in communication with the stimulus generator, wherein the stimulus electrode is adapted to be positioned relative to the myocardial lesion to transmit the sub-threshold electrical stimulus selectively to the myocardial lesion. The example device can also comprise a control unit in communication with the stimulus generator. The control unit is configured to trigger production of the sub-threshold electrical stimulus by the stimulus generator for transmission to the myocardial lesion. The myocardial lesion of the subject treated can include, but is not limited to, a fibrotic lesion, an arrhythmia, or an ischemic area of the myocardium.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 15 is a schematic illustration of a pulse waveform cycle.

DETAILED DESCRIPTION

The following detailed description should be read with reference to the drawings in which similar elements in different drawings are numbered the same. The drawings, which are not necessarily to scale, depict illustrative embodiments and are not intended to limit the scope of what is claimed.

Provided are devices and methods for treating a subject having, or at risk of developing, a myocardial condition. Myocardial conditions include myocardial lesions such as myocardial scarring or myocardial infarction. Myocardial conditions also include other lesions such as areas or regions of myocardial ischemia, with or without infarction, or scarring, and cardiac electrical abnormalities such as arrhythmias. The term subject includes human and non-human animals. The term does not denote a particular age or sex. Subjects include human and veterinary patients. Subjects having acute coronary syndrome (ACS) or a coronary artery bypass graft can be predisposed to cardiac ischemia and to other myocardial lesions.

Figure 1:
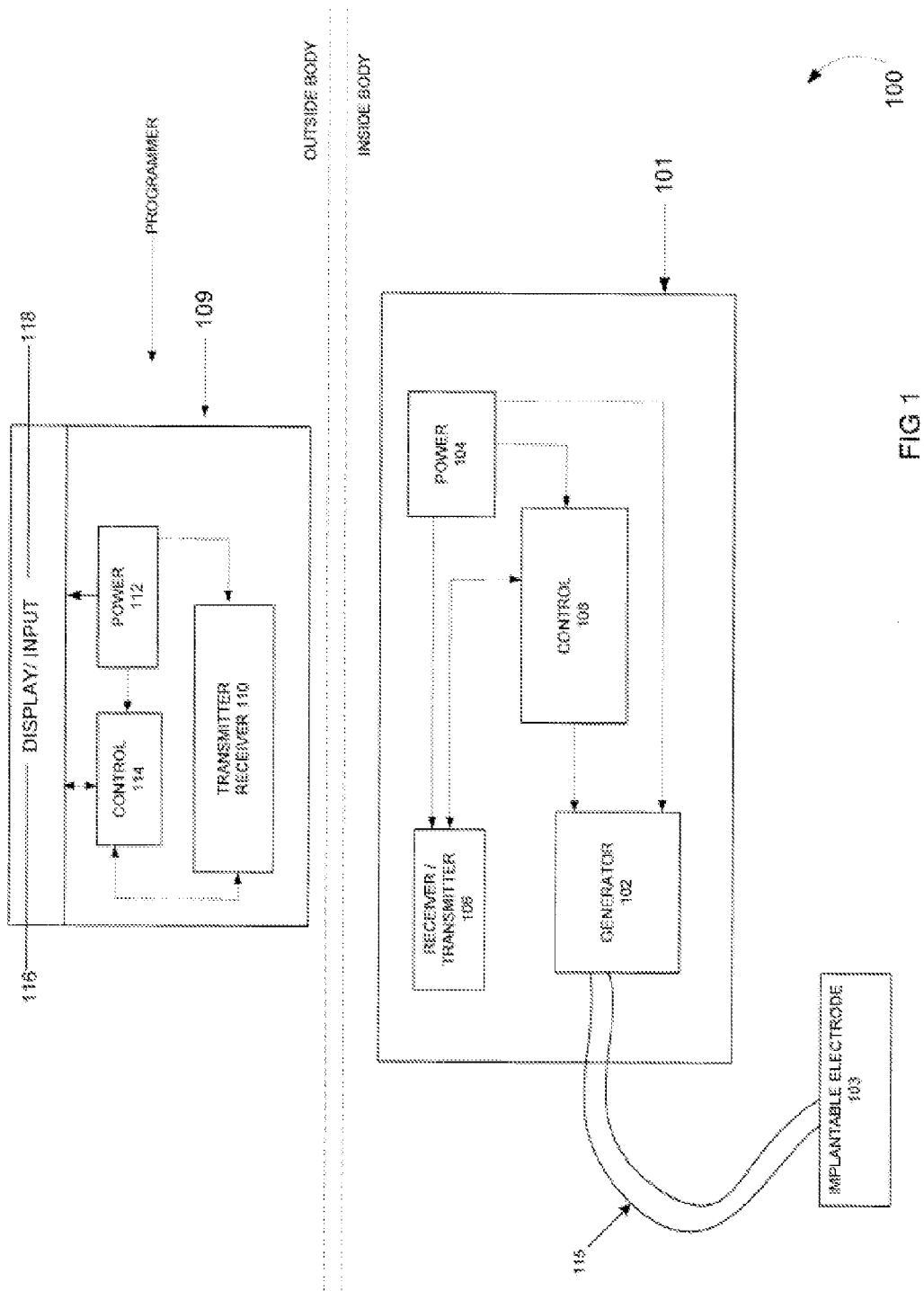
FIG. 1 is a schematic diagram illustrating an example device for treating a myocardial condition.

FIG. 1 illustrates an example device 100 for treating a subject having a myocardial lesion. The device 100 comprises a stimulus generator 102 adapted to produce a sub-threshold electrical stimulus for transmission to the myocardial lesion. The example device 100 can further comprise a stimulus electrode 103 in communication with the stimulus generator 102. The stimulus electrode 103 can be adapted to be positioned relative to the myocardial lesion to transmit the sub-threshold electrical stimulus selectively to the myocardial lesion. The stimulus generator 102 can be in communication with the stimulus electrode 103 by means of a conducting element 115. The example device 100 can also comprise a control unit 108 in communication with the stimulus generator 102. The control unit 108 can include control circuitry and can be configured to trigger production of the sub-threshold electrical stimulus by the stimulus generator 102 for transmission to the myocardial lesion.

A sub-threshold stimulus is a stimulus that is inadequate to produce (evoke) an electrical pacing response in a subject's heart. Optionally, the stimulus generator 102 is configured to produce one or more sub-threshold electrical pulses. For example, the stimulus generator can be configured to produce a plurality of electrical pulses at a frequency of about 1 Hertz (Hz) or greater, including for example, 1, 2, or 4 Hz. Optionally, a plurality of electrical pulses are generated at a frequency of between about 1 Hz and about 20 Kilohertz (kHz).

The pulse can be a pulse waveform with a pulse of amplitude greater than zero ("mark") for a certain period of time followed by an amplitude of about zero ("space") for a certain period of time. A schematic illustration of a pulse waveform cycle is shown in FIG. 15. The total time period of the mark and space equal one cycle of the waveform. The repetition rate of the total waveform (the mark and the space) is the frequency. The time period of the mark and the time period of the space do not have to be equal. The shape of the pulse typically is square but can also be other shapes such as sawtooth (triangular) or similar ramping shapes.

For example the pulse waveform can comprise a pulse (the mark) of about 1.0 volt (V) amplitude for a duration of about 0.50 milliseconds (ms) followed by an amplitude of about 0V for about 999.5 ms (the space) with the waveform repeating thereafter for some time period, thus yielding a frequency of about 1 Hz. Additionally, the pulse waveform can comprise a pulse (the mark) of about 1.0V amplitude for a duration of about 0.10 ms followed by an amplitude of about 0V for about 999.9 ms (the space) with the waveform repeating thereafter for some time period, thus yielding a frequency of about 1 Hz. Various durations, amplitudes, and resulting frequencies are possible using the general parameters described herein.

The pulse (the mark in the waveform) duration can be selected from a range of about 0.05 ms to about 0.50 ms. For example, the pulse can be about 0.50 ms, about 0.10 ms, about 0.05 ms or less. The amplitude of a pulse (the mark in the waveform) can be selected from a range of about 2.0V to about 0.5V. For example, a pulse (the mark in the waveform) can have an amplitude of about 2.0V, about 1.0V or less, about 0.8V or less, or about 0.5V, or less. The amplitude of the pulse (the mark in the waveform) can be selected from about 0.5V to a value greater than zero.

Similarly, the pulse is associated with an electric field that can vary. The pulse (the mark in the waveform) can have an electric field with a current density selected from a range of about 20 milliamps per centimeter (mA/cm), to about 5 mA/cm, or less. For example, the electric field can be 20 mA/cm, to about 5 mA/cm, or less.

The stimulus can be transmitted to the subject's myocardium throughout the cardiac cycle. The stimulus can be transmitted to the subject's myocardium for hours, days, weeks, months or years. Optionally, the stimulus is transmitted for a predetermined duration, for example, over an hour, day, week, month or year, after which duration of the stimulation transmission can be terminated. Optionally, a sub-threshold stimulus can be re-transmitted for a second predetermined duration, which can also be over a period of an hour, day, week, month or year.

To achieve production of a sub-threshold stimulation pulse, the amplitude and duration of the pulse can be monitored. For example, the electrical activity of the heart can be monitored and the characteristics of the electrical stimulus can be modified to achieve sub-threshold stimulation. Thus, amplitude and duration can be altered or modified to achieve sub-threshold stimulation based on monitored electrical activity of the heart. Optionally, these amplitudes and durations can be altered in opposite directions to achieve a sub-threshold stimulus.

A stimulus electrode 103 can be positioned relative to the myocardial lesion, area of ischemia, potential area of ischemia or lesion, or at the origin of a cardiac arrhythmia to transmit the sub-threshold electrical stimulus selectively to the myocardial lesion, to areas of myocardial ischemia, areas of arrhythmia, or areas predisposed to these conditions. Optionally, the myocardial lesion of the subject treated can include, but is not limited to, a fibrotic lesion, an arrhythmia, or an ischemic area of the myocardium. The stimulus electrode is positionable in overlying registration with the myocardial lesion or a portion thereof. Optionally, the stimulus electrode is positionable in direct electrical contact with the myocardial lesion.

Accurate placement of the stimulus electrode 103, such that selective stimulation is achieved, can be based on the identification or localization of myocardial conditions in the subject's heart. Cardiac lesions and conditions can be identified and localized using medical diagnostic procedures. For example, the heart can be visualized using a variety of medical imaging modalities, such as ultrasound, or the heart can be directly visualized using a surgical approach. Visualization or imaging can be used to identify lesions in the heart or areas of the heart that are likely to become damaged due to ischemia. Histology, for example from a myocardial biopsy, can also be used to identify locations for placement of a stimulus lead 103.

The electrical activity of the heart can also be monitored to localize cardiac lesions, ischemia, or arrhythmia origins. Optionally, a twelve-lead ECG can be used to monitor the electrical activity of the heart and to localize areas so that the stimulus electrode 103 can be accurately positioned.

Figure 4:
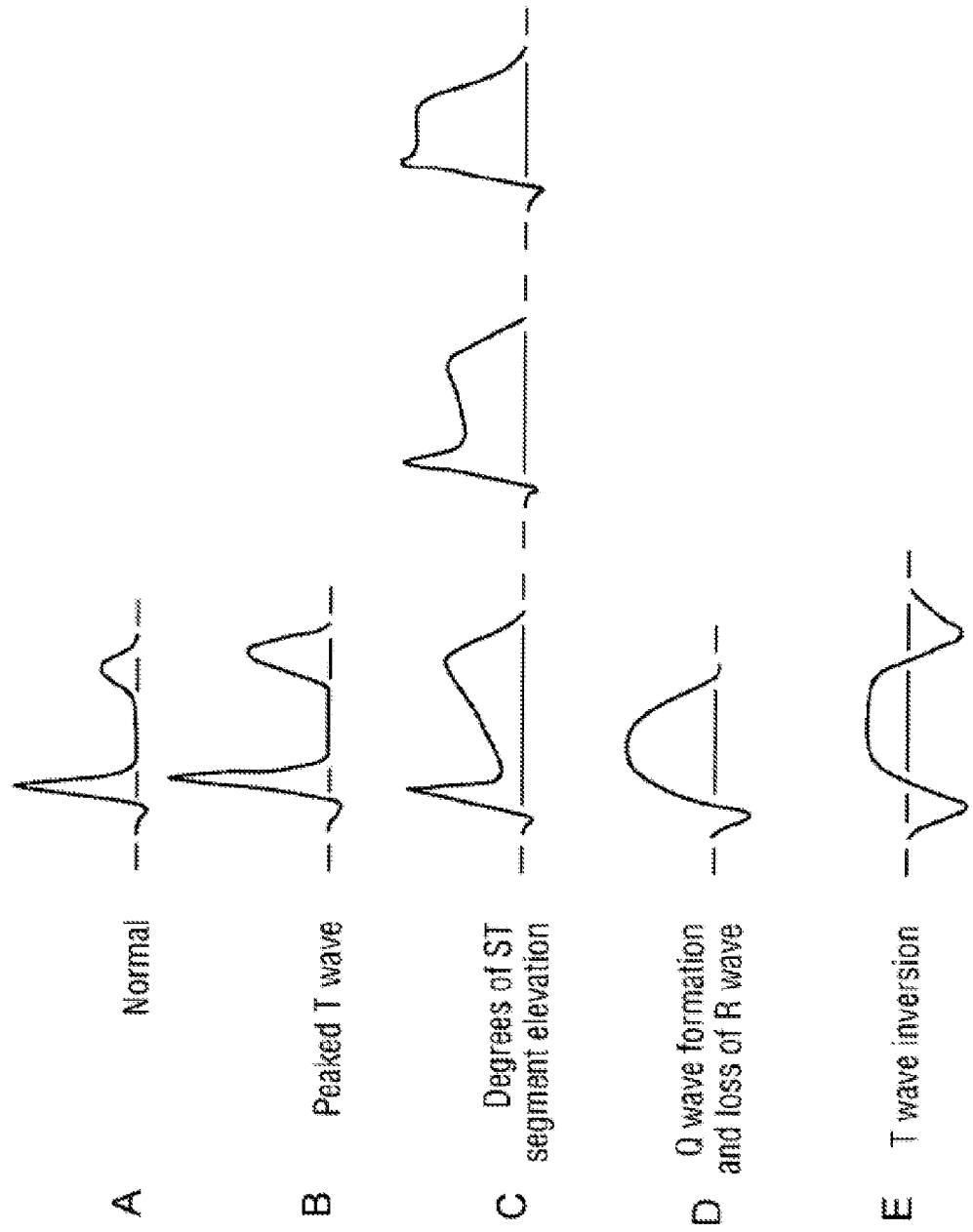
FIG. 4 (A-E) are illustrations of cardiac electrical activity patterns that can be used to locate a position for placement of an electrode relative to a myocardial condition.

FIG. 4 (A-E) show abnormalities that can be identified to direct positioning of the stimulus electrode 103. For example, identification and localization of a peaked T wave (FIG. 4B), ST segment elevation (FIG. 4C), Q wave formation and loss of R wave (FIG. 4D), and T wave inversion (FIG. 4E) from a twelve-lead ECG are myocardial electrical features that can be used to identify and locate cardiac conditions, including lesions and ischemic areas. Based on these identifying parameters, a stimulus electrode 103 can be positioned relative to the myocardium such that the myocardial lesion, area of ischemia or possible ischemia, and/or the arrhythmic origin can be selectively stimulated.

Referring again to FIG. 1, the device 100 can further comprise a power unit 104 and a receiver/transmitter unit 106. The control unit 108, the stimulus generator 102, the power unit 104, and the receiver/transmitter unit 106 can all be enclosed in a casing 101.

The casing 101 can be implanted within a subject similar to the casing of a typical pacemaker. The power unit 104 is in communication with the control unit 108 and the stimulus generator 102. Thus, when directed by the control unit 108, the stimulus generator 102 can transmit an electrical stimulus along a lead 115 to the stimulus electrode 103. The stimulus electrode 103 can be positioned to deliver the stimulus selectively to a desired location of the myocardium. The power unit 104 can also provide power to the control unit 108 and the receiver transmitter unit 106. The power unit 104 is optionally a battery such as those commonly used in implantable medical devices like pacemakers.

The receiver/transmitter unit 106 can comprise circuitry for remotely transmitting data to an outside processing unit 109. Similarly, the receiver/transmitter unit 106 can comprise circuitry for receiving data from an outside processing unit 109. Using the receiver/transmitter unit 106 and the remote processing unit 109, the device 100 can be controlled and monitored from outside the subject's body. In addition to a transmitter/receiver 110, the remote processing unit 109 can comprise a power unit 112 and a control unit 114. The remote processing unit, can also comprise a display 116 and a input unit 118. Using the remote processing unit an operator, such as a medical professional, can adjust the operating parameters of the device 100. For example, the characteristics of the electrical stimulus produced by the stimulus generator 102 can be modified remotely using the processing unit 109.

Figure 2:
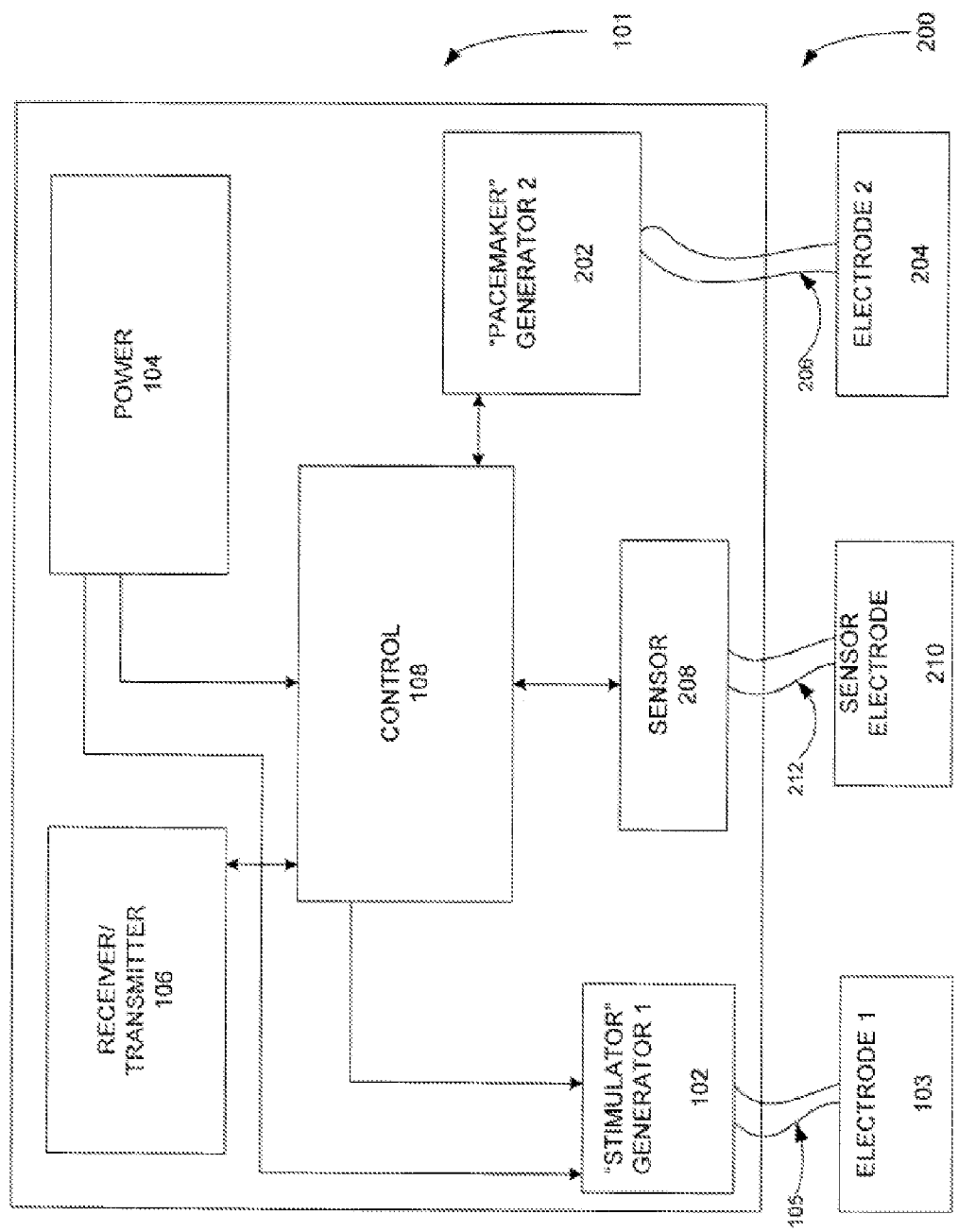
FIG. 2 is a schematic diagram illustrating an example device for treating a myocardial condition.

FIG. 2 is a schematic illustration of an example device 200. The device 200 can be used to treat a cardiac condition, lesion, arrhythmia, or ischemia of the myocardium. The device 200 can comprise a sensor electrode 210 adapted to be positioned relative to the subject's myocardium to sense electrical activity in the myocardium and a sensor unit 208 in communication with the sensor electrode 210. The sensor unit 208 is configured to process electrical signals sensed by the sensor electrode 210. The sensor unit can be in communication with the control unit 108. The control unit 108 can be configured to trigger production of the sub-threshold electrical stimulus based on a predetermined characteristic of the sensed electrical activity of the myocardium. For example, detection of a sinus rhythm of a predetermined duration can be used to trigger the sub-threshold electrical stimulus. Optionally, a sinus rhythm detected for about 30 seconds or more can be used to trigger the sub-threshold electrical stimulus. The control unit 108 can also be configured to refrain from triggering production of the sub-threshold electrical stimulus based on a predetermined characteristic of the sensed electrical activity of the myocardium. For example, detection of ventricular tachycardia can be used to cause refrain of triggering of the sub-threshold electrical stimulus.

The device 200 can further comprise a pacing generator or pacemaker generator 202 adapted to produce a supra-threshold electrical stimulus for transmission to a portion of subject's myocardium and a pacing electrode 204 in communication with the pacing generator. A supra-threshold stimulus can be achieved by increasing the amplitude and/or duration of the stimulus pulse. For example, a low amplitude pulse of a long duration can be supra-threshold. Conversely, a short duration pulse of a large amplitude can also be supra-threshold.

The pacing electrode 204 is adapted to be positioned relative to the subject's myocardium to transmit the supra-threshold electrical stimulus to the subject's myocardium to pace the subject's heart. The pacing generator 202 can be in communication with the control unit 108 such that the control unit 108 can trigger production of the supra-threshold electrical stimulus by the pacing generator 202 for transmission to and pacing of the subject's myocardium.

Thus, the device 200 can comprise a stimulus generator 102 and stimulus electrode 103 as described in relation to FIG. 1. In addition, as shown in FIG. 2, the device 200 can comprise a pacing function for pacing the subject's heart. Pacing of the subject's heart can be through a pacemaker or pacing electrode 204 connected by a lead 206 to a pacing generator 202. The device 200 can therefore act to provide a sub-threshold stimulus and a super-threshold stimulus for pacing the heart.

Figure 3:
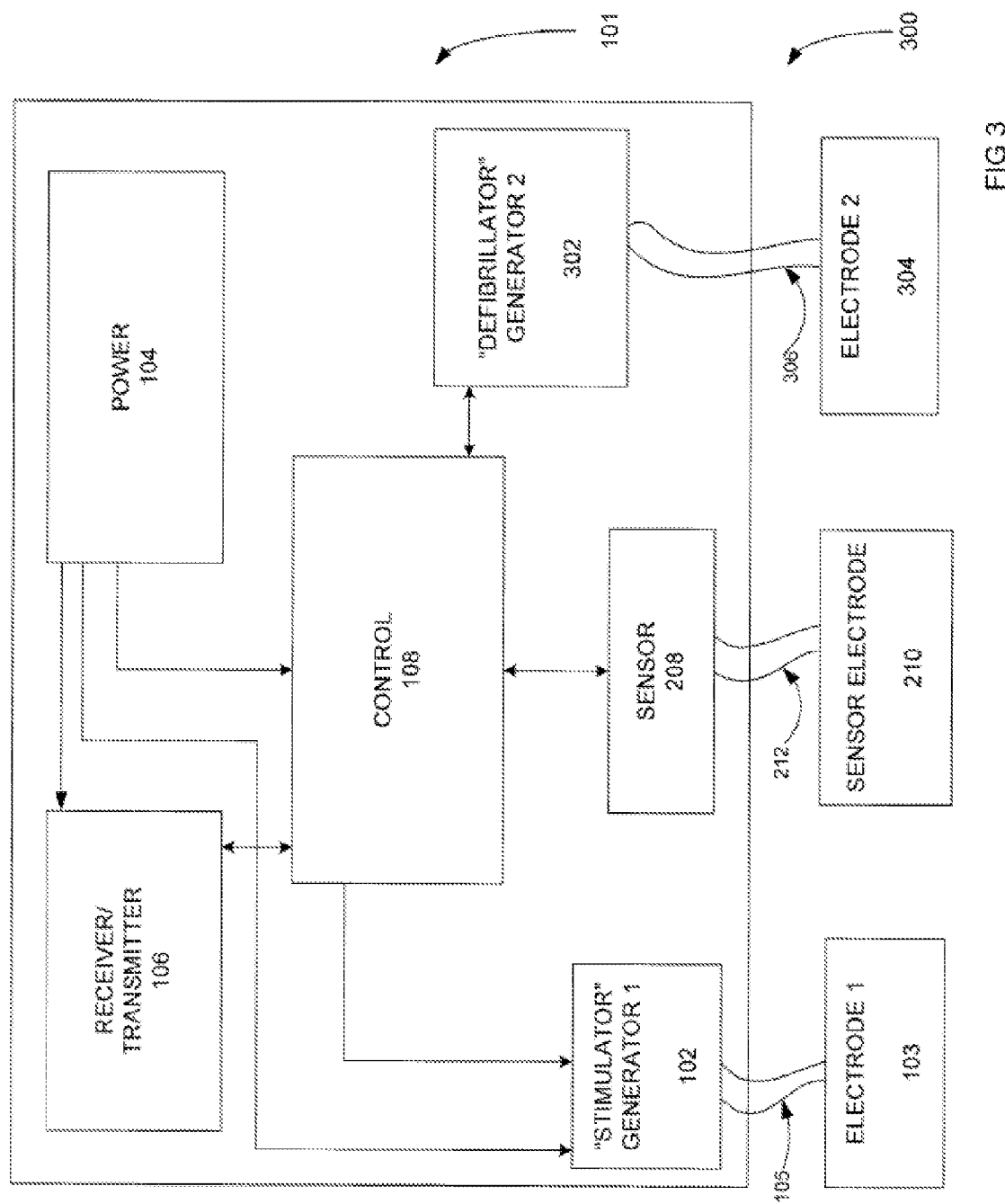
FIG. 3 is a schematic diagram illustrating an example device for treating a myocardial condition.

As shown in FIG. 3, an example device 300 can further comprise a defibrillator generator 302 adapted to produce a defibrillating electrical stimulus for transmission to a portion of subject's myocardium. The defibrillator generator 302 can be in communication with a defibrillator electrode 304. The defibrillator electrode 304 can be positioned relative to the subject's myocardium to transmit the defibrillating electrical stimulus to the subject's myocardium to pace the subject's heart. Thus, as shown in FIG. 3, an example device 300 can comprise pacing functions, sub-threshold stimulation functions, and defibrillation functions. In this regard, the example device 300 is a combined pacemaker/defibrillator device with the additional sub-threshold stimulation capability provided for treatment (e.g. healing or prevention) of myocardial conditions.

Also provided are methods of treating a subject having a myocardial condition. For example, subjects having a myocardial lesion, ischemic myocardium, and/or arrhythmia can be treated. In some examples, subjects predisposed to any of these conditions can also be treated. For example, subjects having acute coronary syndrome (ACS) or having a coronary artery bypass graft (CABG) are predisposed to myocardial ischemia and myocardial infarction. These subjects can be treated to prevent ischemic injury including myocardial infarction by applying sub-threshold stimulation selectively to areas of the myocardium that are at increased risk of ischemia or ischemic damage. Such areas can be identified based on the subject's condition and using cardiac diagnostic procedures. The methods can be performed using the example devices described herein.

For example, a method for treating a subject having a myocardial lesion comprises positioning an electrode relative to the myocardial lesion so that an electrical stimulus can be transmitted selectively to the myocardial lesion. A sub-threshold electrical stimulus can be selectively transmitted to the myocardial lesion. Optionally, the myocardial lesion can be a scar, a myocardial infarction, an alcohol ablation lesion or a cryoablation lesion. The lesion can be an area of myocardial ischemia.

Thus, for example, further provided is a method for treating a subject having myocardial ischemia comprising positioning an electrode relative to an area of myocardial ischemia in the subject's heart so that an electrical stimulus can be transmitted selectively to the area of myocardial ischemia. A sub-threshold electrical stimulus can be selectively transmitted to the area of myocardial ischemia. The lesion can be a cardiac arrhythmia. A method for treating a subject having a cardiac arrhythmia comprises positioning an electrode relative to the subject's heart so that an electrical stimulus can be transmitted selectively to the myocardium at the anatomic origin of the arrhythmia. A sub-threshold electrical stimulus can be selectively transmitted to the myocardium at the origin of the arrhythmia.

The electrode used to transmit the sub-threshold electrical stimulus can be implanted within the subject. For example, the electrode can be positioned in overlying registration with the myocardial lesion or a portion thereof. Optionally, the electrode can be positioned in direct electrical communication with the myocardial lesion. The sub-threshold stimulus can be applied over time to treat a condition of the cardiac myocardium. The treatment can effectively reduce matrix metalloproteinase (MMP) activity in or about the myocardial lesion. The treatment can also prevent or reduce thinning of the myocardial lesion. Thus, in lesions with anatomical pathology, the sub-threshold electrical stimulus can alter a material characteristic of the myocardial lesion. For example, stiffness, tensile strength and compliance of the lesion can be altered. The sub-threshold electrical stimulus can also be used to increase collagen in or about the myocardial lesion.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope except as and to the extent that they are included in the accompanying claims. Efforts have been made to ensure accuracy with respect to numbers (e.g., amounts, temperature, etc.), but some errors and deviations should be accounted for.

Example 1

Left Ventricular Myocardial Fibroblasts (LVMF)

LVMFs are the most abundant cell type in myocardium and they form a cellular network throughout myocardium. LVMFs synthesize and release matrix metalloproteinases (MMPs), tissue inhibitors of metalloproteinases (TIMPs) and collagen. Release can be modulated by cytokines and other signaling molecules. Mechanical perturbation (stretch) of LVMFs can induce MMP release. LVMFs also have electrical properties. For example, LVMFs have interconnectivity with other LVMFs and myocytes through gap junctions. LVMF's possess electrogenic processes, including voltage-gated ionic channels.

LVMFs were obtained using the outgrowth technique from biopsy (2 mm×2 mm×2 mm) sections from the LV free wall of a pig. LVMFs were cultured and LVMFs from passages 2-5 were plated onto a 4-well chamber (plastic base) at a density of $60 \times 10^5$ cells/well. Once the LVMFs were 80% confluent, the medium was changed to a serum-free medium and cells incubated for 24 hours. Carbon (graphite) electrodes were placed at the ends of each chamber and the LVMFs electrically stimulated using 5 ms, 2 mA, 4 V/cm pulses in each chamber. The polarity of the electrical pulse was alternated with every beat to prevent buildup of electrolytic products. The cells were stimulated at the designated frequency for 24 hours, following which the cell pellet and media were collected for biochemical assays.

Figure 5:
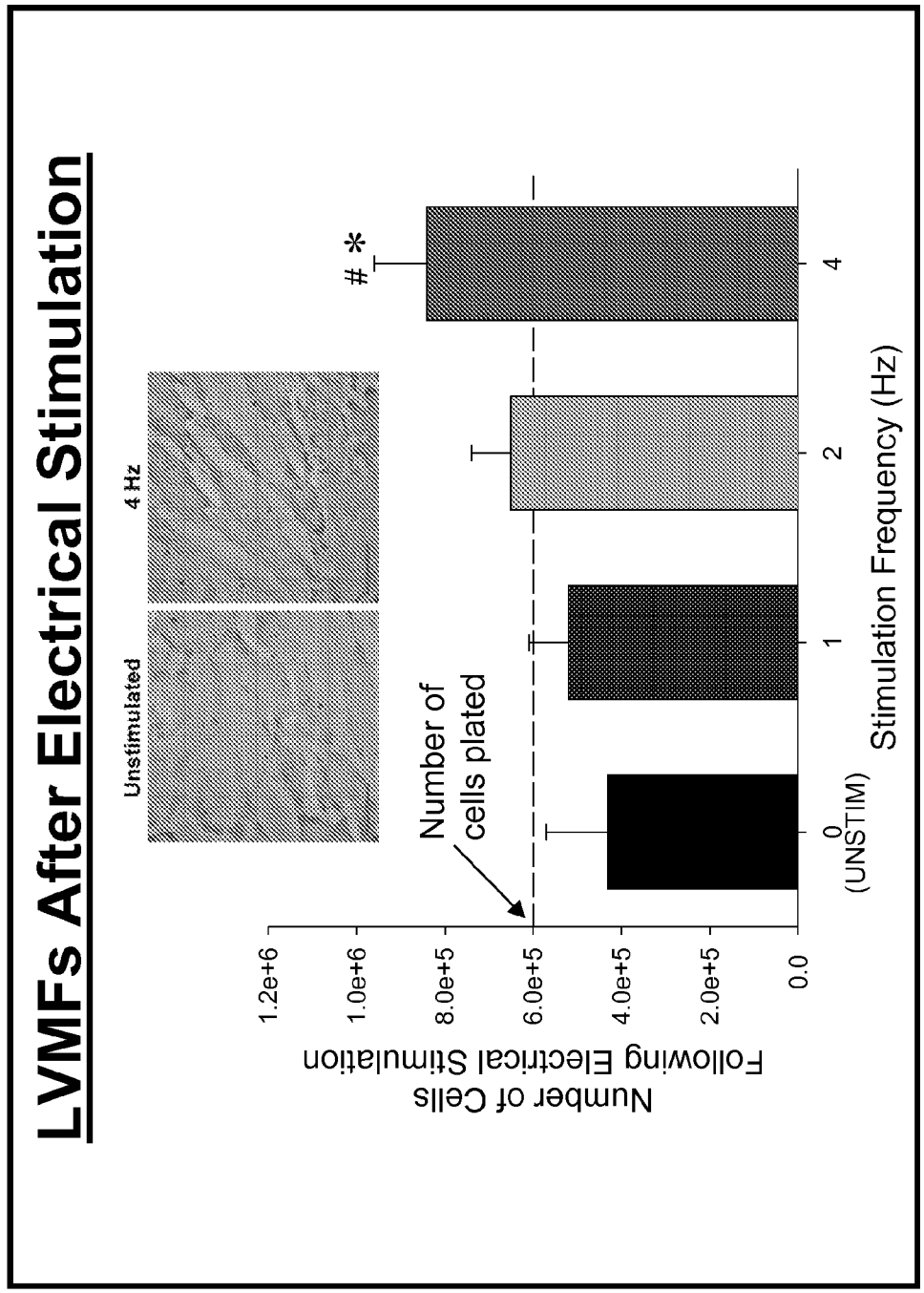
FIG. 5 illustrates the number of left ventricular myocardial fibroblasts in unstimulated (UNSTIM) and stimulated assay samples (1, 2, or 4 Hz).

As shown in FIG. 5, following 24 hours of electrical stimulation, LVMFs retained morphological characteristics. There was a larger number of LVMFs in the wells stimulated at 4 Hz compared to the unstimulated (UNSTIM, 0 Hz) wells. # $p<0.05$ vs. UNSTIM, *$p<0.05$ vs. the plated number of $6 \times 10^5$ cells/well.

Figure 6:
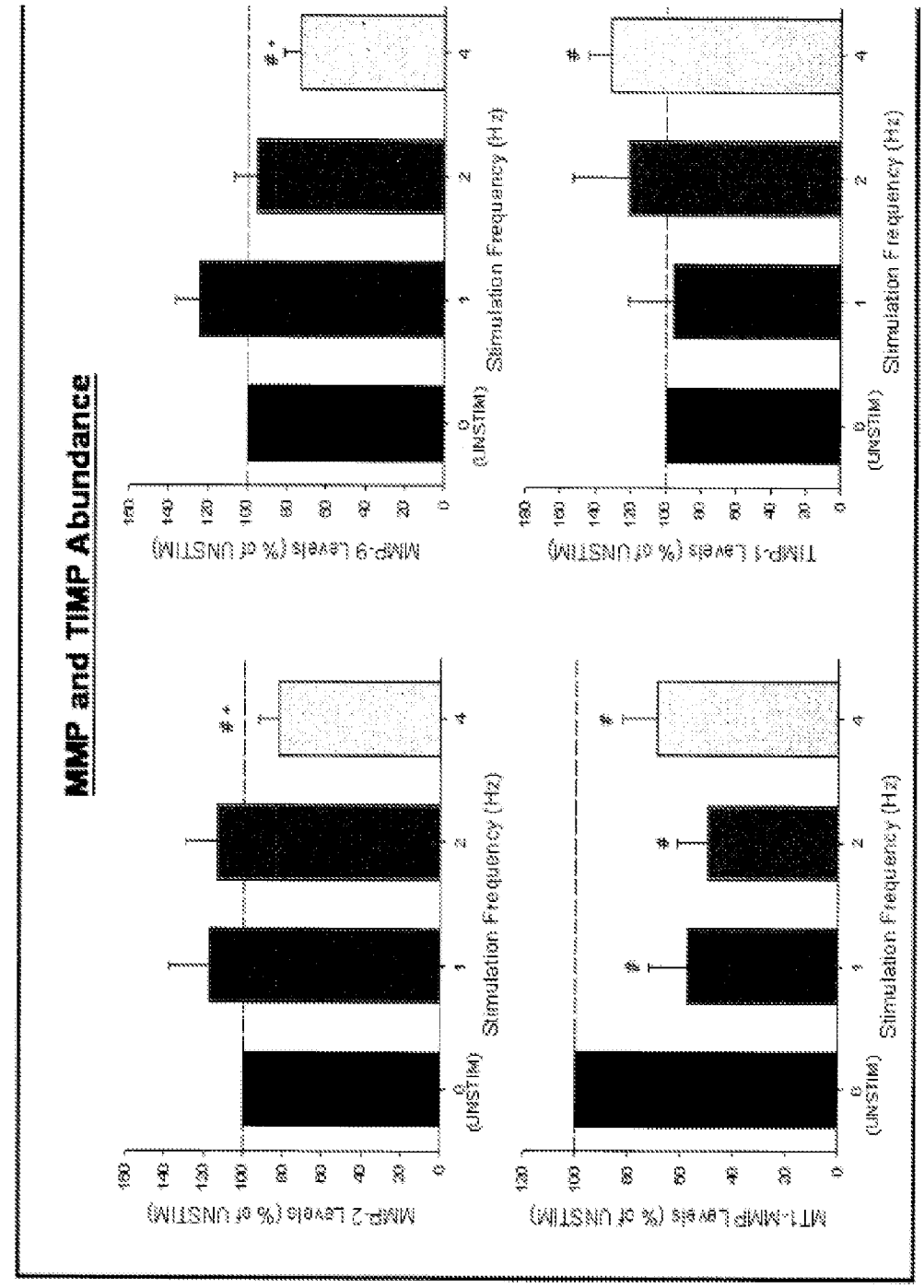
FIG. 6 illustrates matrix metalloproteinase (MMP) levels and tissue inhibitors of metalloproteinase (TIMP) levels in unstimulated (UNSTIM) and stimulated (1, 2, or 4 Hz) assay samples of left ventricular myocardial fibroblasts (LVMFs).

FIG. 6 shows results of MMP-2 and MMP-9 levels. Levels were determined using gelatin zymography and MT1-MMP and TIMP-1 levels were determined by immunoblotting. Positive controls were included for each assay. Integrated optical densities from each assay were divided cell number and then normalized to values obtained for the UNSTIM group (100%). #$p<0.05$ vs UNSTIM, +$p<0.05$ vs. 1 Hz.

Figure 7:
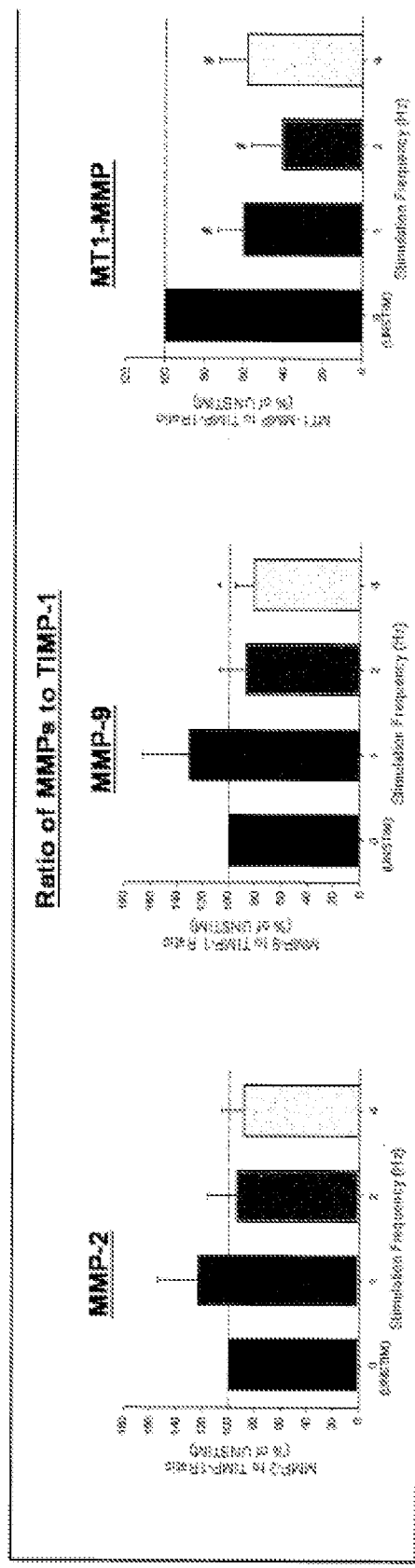
FIG. 7 illustrates the ratio of matrix metalloproteinases MMPs to tissue inhibitors of metalloproteinases TIMP-1 in unstimulated (UNSTIM) and stimulated (1, 2, or 4 Hz) LVMF assay samples.

To determine whether and to what degree electrical stimulation caused a frequency-dependent change in the stoichiometry between MMPs and TIMP-1, ratios of the MMPs and TIMP-1 were computed and are shown in FIG. 7. These ratios were normalized to values obtained for the UNSTIM group (100%). # $p<0.05$ vs. UNSTIM, +$p<0.05$.

Example 2

Matrix Metalloproteninases (MMPs) and Myocardial Remodeling

MMPs are endopeptidases that degrade components of the extracellular matrix. MMP activity is endogenously regulated by the tissue inhibitors of the metalloproteinases (TIMPs). Specific MMPs and TIMPs are identified within the myocardium and changes in the MMP/TIMP system are associated with myocardial remodeling in several cardiac disease states. Fibroblasts/myofibroblasts are present in high proportion in myocardial infarction scars and these cells synthesize and release MMPs, TIMPs and collagen. The example shows that sub-threshold stimulation (LHFS) was instituted within a formed MI scar. The stimulation altered regional geometry, reduced interstitial MMP activity, increased regional collagen content, and increased regional myocardial stiffness.

Figure 8:
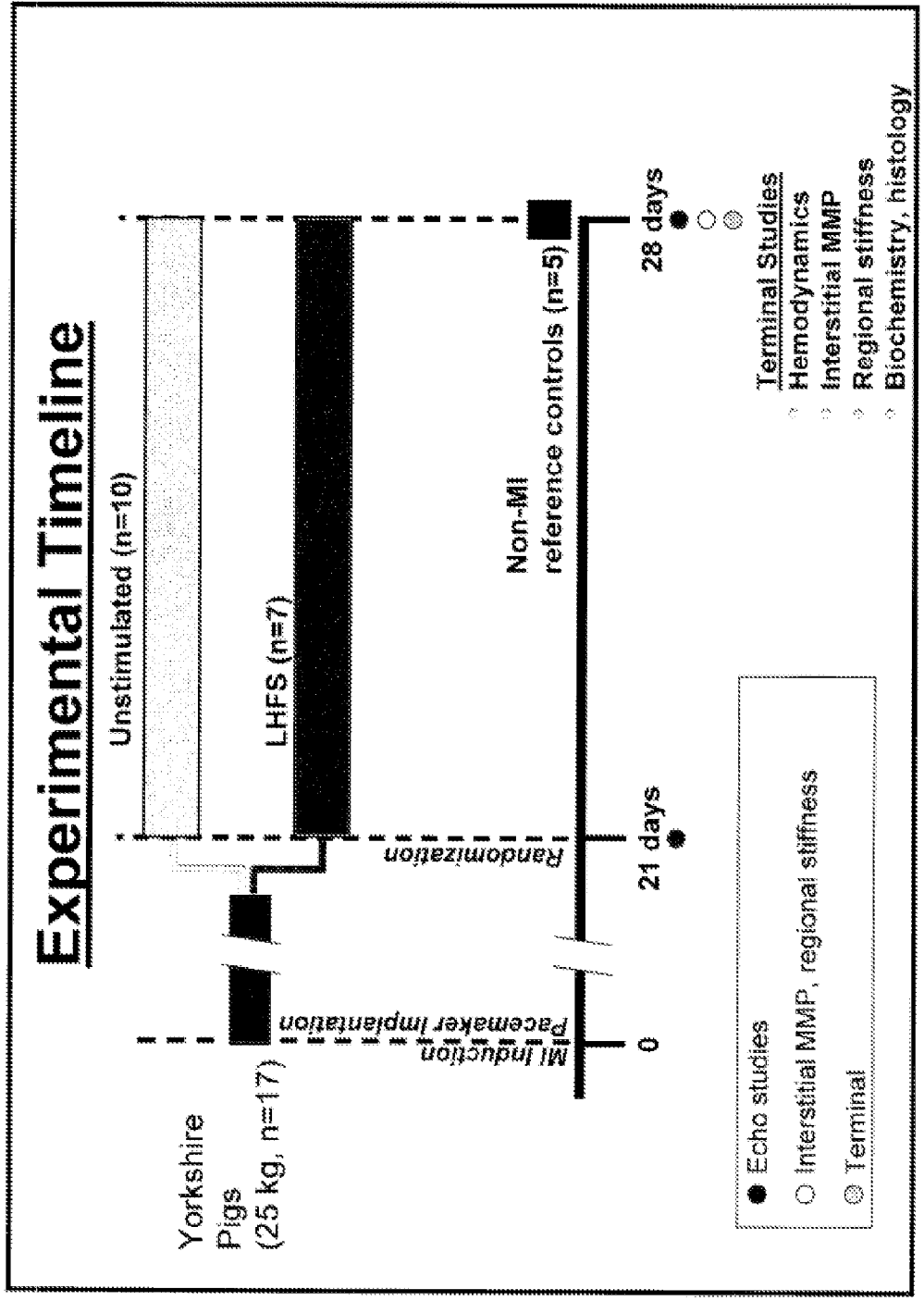
FIG. 8 illustrates a timeline for treatment of myocardial infarction lesions in a pig model using sub-threshold electrical stimulation (LHFS) and no stimulation.

As illustrated in FIG. 8, myocardial infarction (MI) was induced in 17 adult pigs by coronary ligation. Pacemakers were implanted at the time of MI induction in the center of the MI region. At 21 days post-MI, pigs were echoed and randomized into a groups that were unstimulated (n=10) or that were given sub-threshold localized high frequency electrical stimulation (LHFS) (VOO pacing, 240 bpm, 0.8V, 0.05 ms; n=7). Terminal studies were performed at 28 days post-MI. The studies included in vivo echo, interstitial MMP activity, and stiffness. Biochemistry testing for MMP-2, MMP-9, and TIMP-1 levels was also performed. Histology testing was also performed for collagen content.

Figure 9:
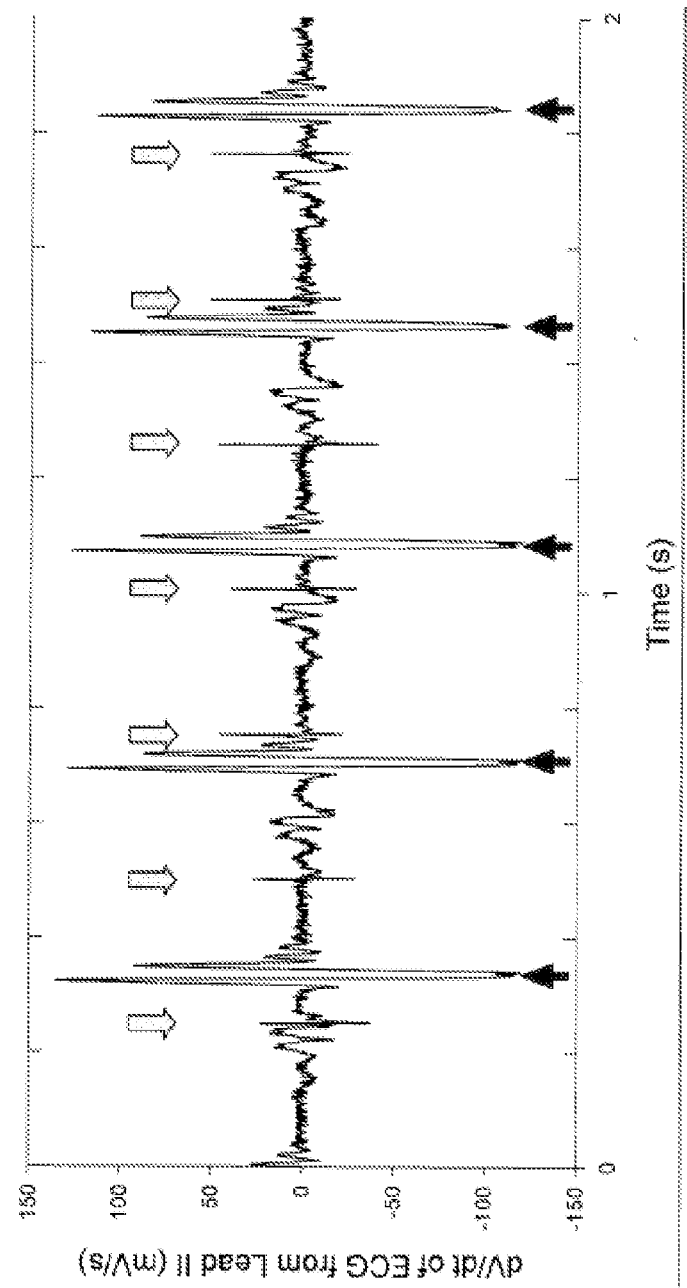
FIG. 9 shows results of an ECG recording with localized stimulation with sub-threshold electricity in a pig model.

FIG. 9 illustrates results of an ECG recording with localized stimulation with sub-threshold electricity in a pig model. FIG. 9 illustrates first derivative of the ECG lead II signal showing the pacemaker pulses (top arrows) and the sinus rhythm-originated QRS complexes (lower arrows).

Figure 10:
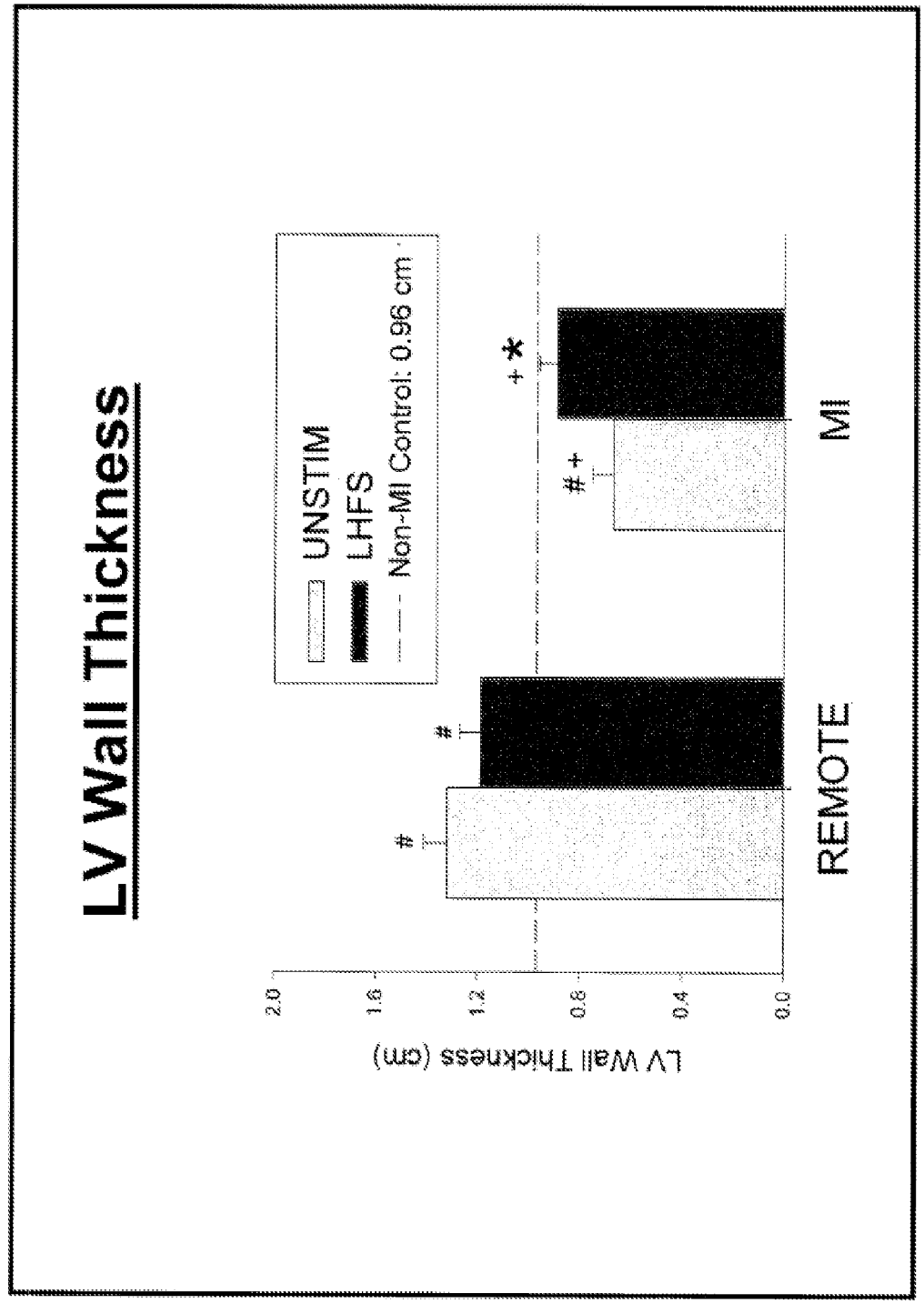
FIG. 10 illustrates left ventricular geometry (wall thickness) for unstimulated (UNSTIM) and sub-threshold stimulation (LHFS) at 28 days post-MI determined by echocardiography in a pig model.

LV geometry at 28 days post-MI was determined by echocardiography. As shown in FIG. 10, although LV end-diastolic diameters were similar between the UNSTIM and LHFS groups, LV wall thickness at the MI region was larger with LHFS compared to the UNSTIM group. # $p<0.05$ vs. Control, +$p<0.05$ vs. Remote Region, * $p<0.05$ vs. UNSTIM.

Figure 11:
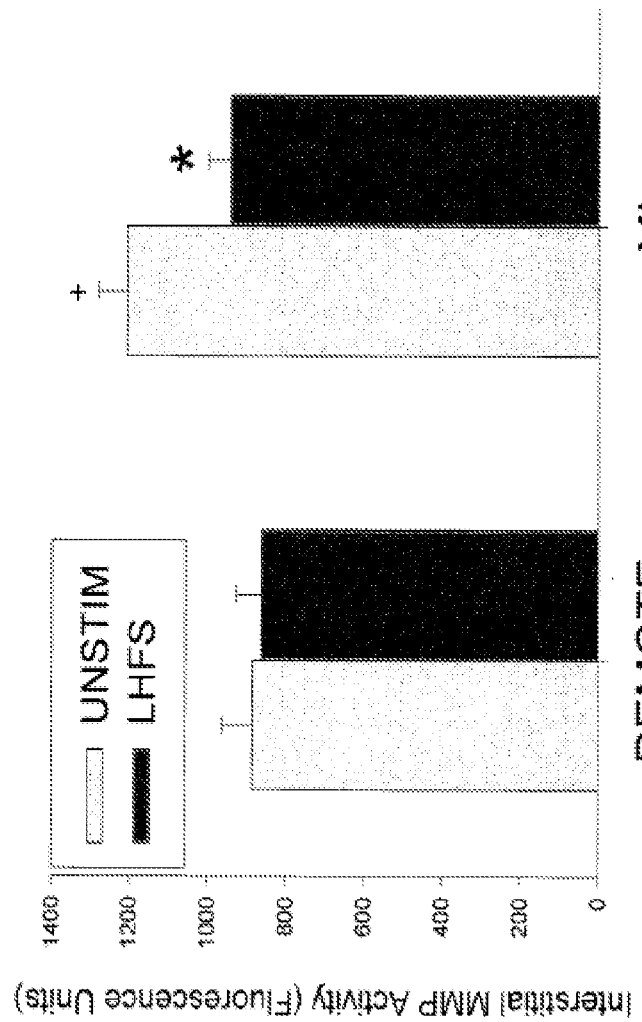
FIG. 11 illustrates interstitial MMP activity for unstimulated (UNSTIM) and sub-threshold stimulation (LHFS) at 28 days post-MI determined by microdialysis in a pig model.

Interstitial MMP activity at 28 days post-MI was determined by microdialysis using a quenched fluorescent substrate that could be cleaved by a number of MMP types. As shown in FIG. 11, there was a significant reduction in interstitial MMP activity with LHFS compared to the UNSTIM group. +$p<0.05$ vs. Remote Region, * $p<0.05$ vs. UNSTIM.

Figure 12:
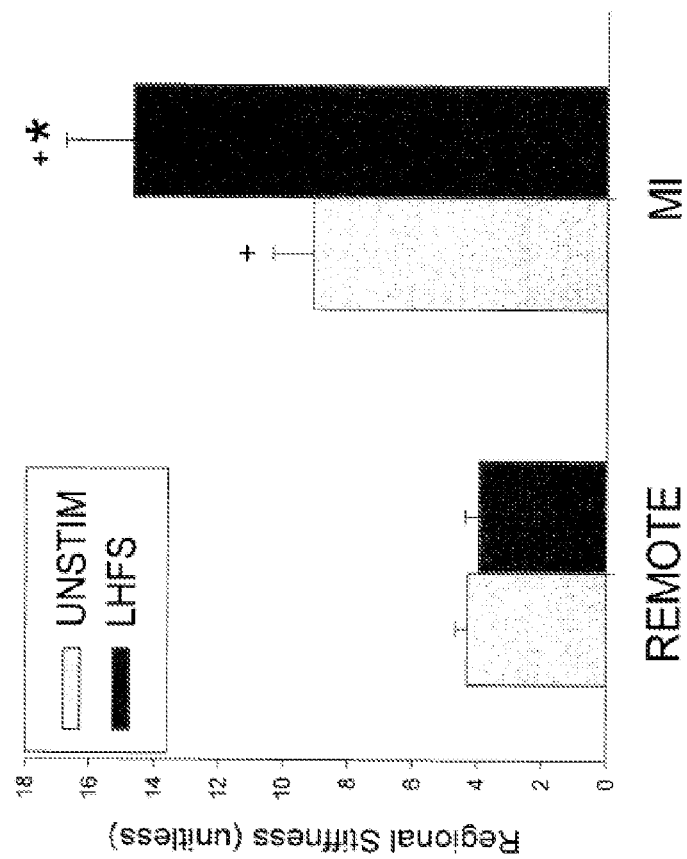
FIG. 12 illustrates regional myocardial stiffness for unstimulated (UNSTIM) and sub-threshold stimulation (LHFS) at 28 days post-MI in a pig model.

Regional myocardial stiffness at 28 days post-MI was determined using piezoelectric crystals instrumented within the MI and remote regions and through beat-to-beat analysis of the end-diastolic pressure—dimension relationship while altering LV preload (transient occlusion of the inferior vena cava). As shown in FIG. 12, regional myocardial stiffness was higher with MI and was further increased with LHFS. +p<0.05 vs. Remote Region, * p<0.05 vs. UNSTIM.

Figure 13:
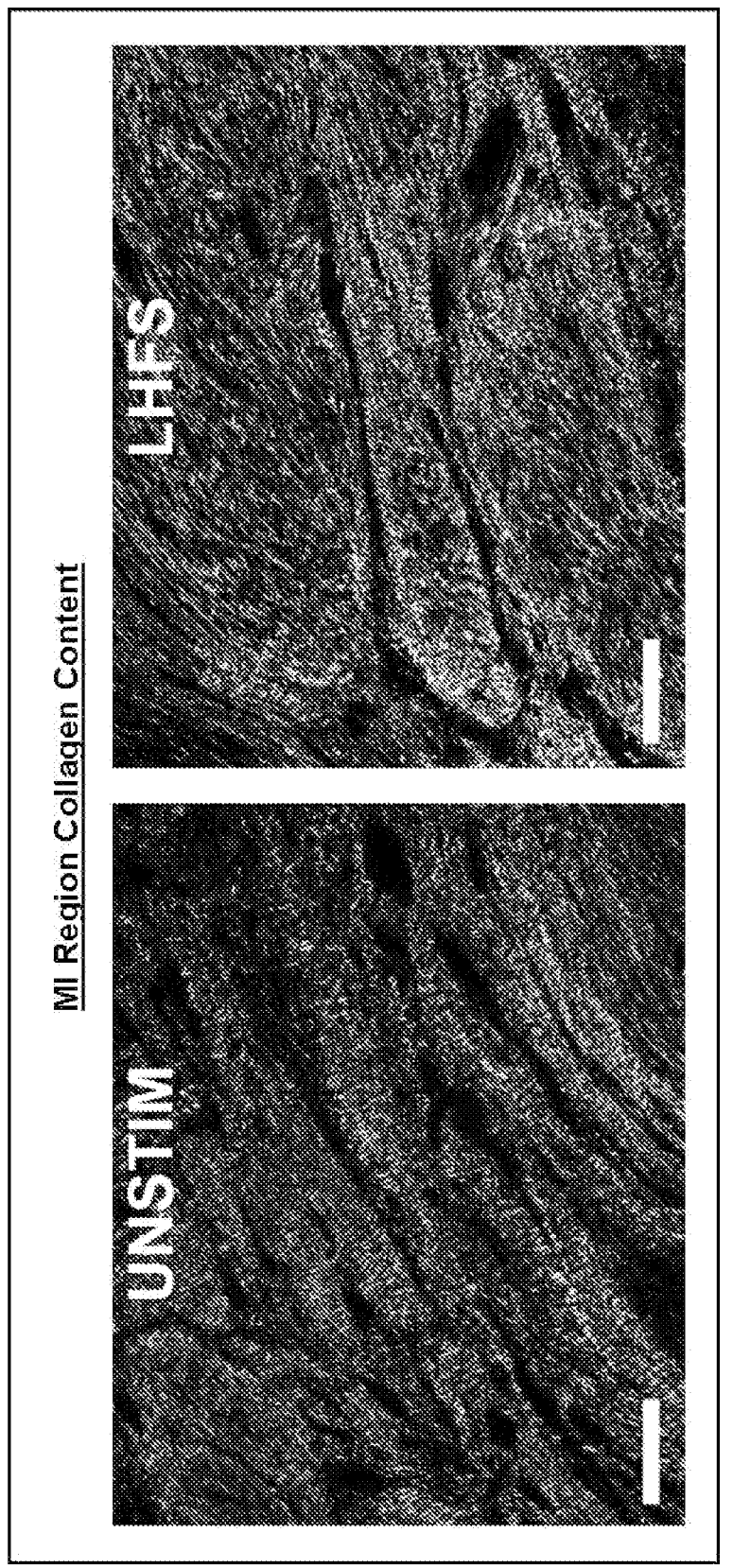
FIG. 13 (A and B) are photomicrographs from the MI region of unstimulated (UNSTIM) (A) and stimulated (LHFS) (B) pigs.

FIG. 13 shows representative photomicrographs of picrosirius red birefringence from the MI region of a pig in which the pacemaker was not activated (UNSTIM, left, FIG. 13A) and from one that underwent LHFS (right, FIG. 13B). There was more collagen in the MI region of the LHFS group than in the UNSTIM group. Scale bars: 200 µm.

Figure 14:
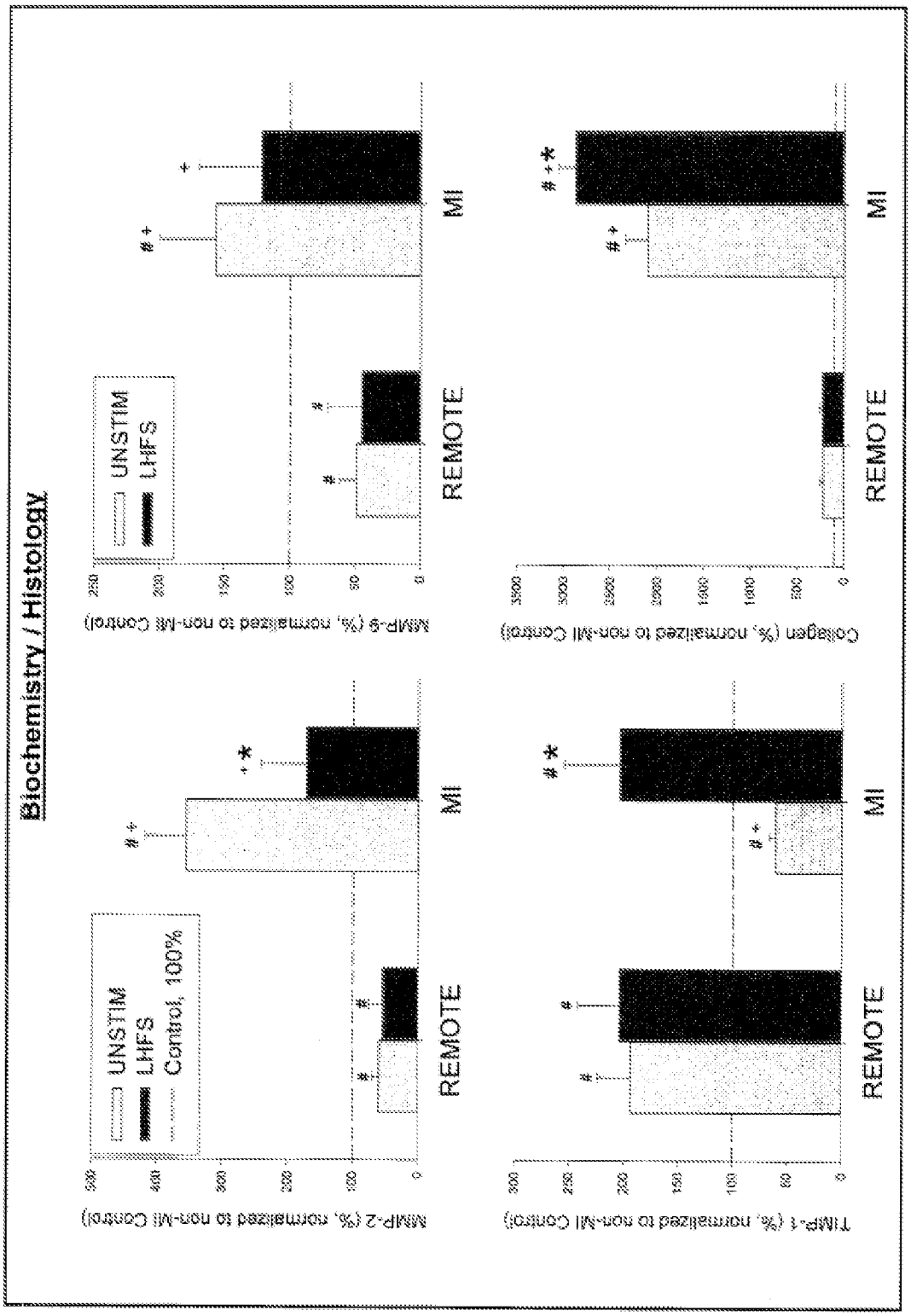
FIG. 14 are histograms showing levels of MMP-2, MMP-9, TIMP-1 and collagen in the remote and MI regions of pigs that were left unstimulated (UNSTIM) or that underwent sub-threshold stimulation (LHFS).

FIG. 14 illustrates levels of MMP-2, MMP-9, TIMP-1, and collagen in the remote and MI regions of pigs that were either left unstimulated (UNSTIM) or underwent LHFS. MMP-2 and MMP-9 levels were determined by substrate-specific zymography, TIMP-1 levels were determined by immunoblotting, and collagen levels were determined morphometrically from picrosirius red stained sections. # p<0.05 vs. Control, +p<0.05 vs. Remote Region, * p<0.05 vs. UNSTIM.

A number of embodiments of the invention have been described. Nevertheless, it will be understood that various modifications may be made without departing from the spirit and scope of the invention. Accordingly, other embodiments are within the scope of the following claims.

What is claimed is:

1. A method for treating a myocardial fibrotic scar in a subject, comprising:
    (a) positioning an electrode in or on the myocardial fibrotic scar so that an electrical stimulus can be transmitted selectively to the myocardial fibrotic scar; and
    (b) transmitting a sub-threshold electrical stimulus selectively to the myocardial fibrotic scar in order to treat the myocardial fibrotic scar.

2. The method of claim 1, wherein the electrode is implanted within the subject in overlying registration with the myocardial fibrotic scar or a portion thereof.

3. The method of claim 1, wherein the electrode is in direct electrical communication with the myocardial fibrotic scar.

4. The method of claim 1, wherein the sub-threshold electrical stimulus is applied throughout a cardiac cycle.

5. The method of claim 1, wherein the electrical stimulus comprises one or more electrical pulse waveforms.

6. The method of claim 5, wherein the pulse waveform has a frequency of about 1 Hertz (Hz) or greater.

7. The method of claim 5, wherein the pulse waveform comprises a mark and the mark has an amplitude of about 2.0 volts (V) or less.

8. The method of claim 5, wherein the pulse waveform comprises a mark and the duration of the mark is about 0.50 milliseconds (ms) or less.

9. A device for treating a myocardial fibrotic scar in a subject, comprising:
    (a) a stimulus generator adapted to produce a sub-threshold electrical stimulus for transmission to the myocardial fibrotic scar;
    (b) a stimulus electrode in communication with the stimulus generator, wherein the stimulus electrode is adapted to be positioned in or on the myocardial fibrotic scar and to transmit the sub-threshold electrical stimulus selectively to the myocardial fibrotic scar; and
    (c) a control unit in communication with the stimulus generator, wherein the control unit is configured to trigger production of the sub-threshold electrical stimulus by the stimulus generator for transmission to and treatment of the myocardial fibrotic scar, wherein the sub-threshold electrical stimulus comprises one or more electrical pulse waveforms comprising a mark with an amplitude of greater than zero with a duration of the mark being less than about 0.50 milliseconds (ms).

10. The device of claim 9, wherein the electrode is positionable in overlying registration with the myocardial fibrotic scar or a portion thereof.

11. The device of 10, wherein the electrode is positionable in direct electrical contact with the myocardial fibrotic scar.

12. The device of claim 9, further comprising:
    (a) a sensor electrode adapted to be positioned relative to the subject's myocardium to sense electrical activity in the myocardium; and
    (b) a sensor unit in communication with the sensor electrode, wherein the sensor unit is configured to process electrical signals sensed by the sensor electrode.

13. The device of claim 12, wherein the sensor unit is in communication with the control unit and wherein the control unit is configured to trigger production of the sub-threshold electrical stimulus based on a predetermined characteristic of the sensed electrical activity of the myocardium.

14. The device of claim 12, wherein the sensor unit is in communication with the control unit and wherein the control unit is configured to refrain from triggering production of the sub-threshold electrical stimulus based on a predetermined characteristic of the sensed electrical activity of the myocardium.

15. The device of claim 9, further comprising:
    (a) a pacing generator adapted to produce a supra-threshold electrical stimulus for transmission to a portion of subject's myocardium; and
    (b) a pacing electrode in communication with the pacing generator, wherein the pacing electrode is adapted to be positioned relative to the subject's myocardium to transmit the supra-threshold electrical stimulus to the subject's myocardium to pace the subject's heart.

16. The device of claim 15, wherein the pacing generator is in communication with the control unit and wherein the control unit is configured to trigger production of the supra-threshold electrical stimulus by the pacing generator for transmission to and pacing of the subject's myocardium.

17. The device of claim 9, further comprising:
    (a) a defibrillator generator adapted to produce a defibrillating electrical stimulus for transmission to a portion of subject's myocardium; and
    (b) a defibrillator electrode in communication with the defibrillator generator, wherein the defibrillator electrode is adapted to be positioned relative to the subject's myocardium to transmit the defibrillating electrical stimulus to the subject's myocardium to pace the subject's heart.

18. The device of claim 9, wherein the stimulus generator is configured to produce the sub-threshold electrical stimulus throughout a cardiac cycle.

19. The device of claim 9, wherein the stimulus generator is configured to produce a pulse waveform having a frequency of about 1 Hertz (Hz) or greater.

20. The device of claim 9, wherein the stimulus generator is configured to produce a pulse waveform comprising a mark having an amplitude of about 2.0 volt (V) or less.

* * * * *